United States Patent [19]

Quinn et al.

[11] 3,956,322

[45] May 11, 1976

[54] DIANHYDRIDES OF BIS-(ORTHODICARBOXYPHENYLOXYPHE-NYL)ACETYLENE AND BIS-(ORTHO-DICARBOXYPHENYLOXY-PHENYL)2,2-DICHLOROETHYLENE

[75] Inventors: Clayton B. Quinn; Frank J. Williams, both of Scotia, N.Y.

[73] Assignee: General Electric Company, Schenectady, N.Y.

[22] Filed: Mar. 14, 1975

[21] Appl. No.: 558,222

[52] U.S. Cl. .............................. 260/346.3
[51] Int. Cl.² ........................... C07D 307/89
[58] Field of Search ...................... 260/346.3

[56] References Cited

UNITED STATES PATENTS 3,879,428  4/1975  Heath et al. ............ 260/346.3

Primary Examiner—Henry R. Jiles
Assistant Examiner—Bernard Dentz
Attorney, Agent, or Firm—Joseph T. Cohen; Jerome C. Squillaro

[57] ABSTRACT

The invention is concerned with dianhydrides derived from either tolane or 1,1-bis(p-hydroxyphenyl)2,2-dichloroethylene. These dianhydrides can be reacted with organic diamines to form polyetherimides useful in the molding art.

4 Claims, No Drawings

DIANHYDRIDES OF BIS-(ORTHODICARBOXYPHENYLOXYPHENYL-)ACETYLENE AND BIS-(ORTHO-DICARBOXYPHENYLOXY-PHENYL)2,2-DICHLOROETHYLENE

This invention is concerned with dianhydrides. More particularly, the invention relates to a novel class of dianhydrides having the formula

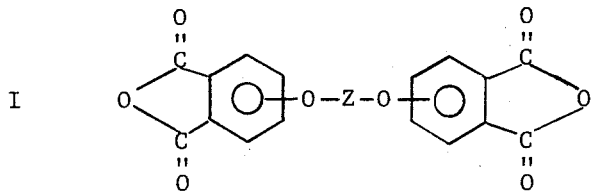

where Z is a member of the class consisting of the

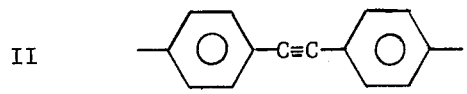

radical and the

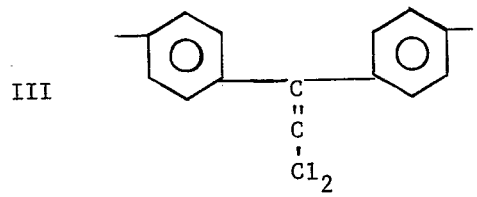

radical.

Two specific dianhydrides coming within the scope of formula I may be identified as (1) an acetylene dianhydride having the formula

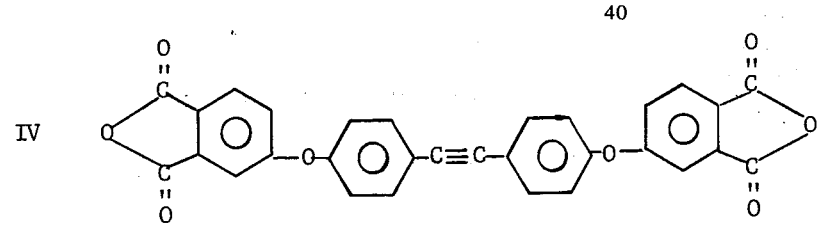

and (2) a dichloroethylene dianhydride having the formula

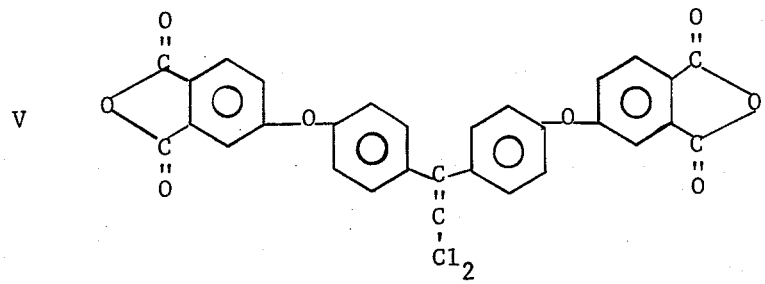

Alternatively, the acetylene and dichloroethylene residues may be attached to the dianhydride portions in the 3-position, depending on the position of the nitro group used as a starting reactant.

Generally, the aforesaid class of dianhydrides may be obtained by effecting reaction between 3-nitro or 4-nitro-N-methylphthalimide having the formula

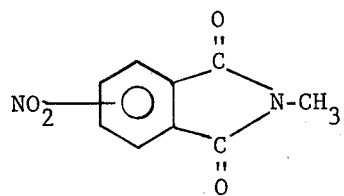

and a member selected from the class consisting of 1,2-bis(p-hydroxyphenyl)acetylene (also referred to as "4,4'-dihydroxy tolane") and 1,1-bis(p-hydroxyphenyl)-2,2-dichloroethylene (hereinafter referred to as "HDE") having the formula

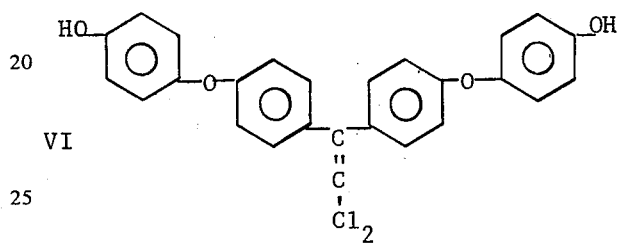

The HDE of formula VI can be prepared in a manner disclosed by J. Trpin and B. G. Zupancic, Monatschafte fuer Chemie, 100, 114 (1969). The 4,4'-dihydroxytolane used to make the corresponding dianhydride can be prepared in accordance with the process described by M. H. Hubacher, J. Org. Chem., 24, 1949 (1959).

We have found that the reaction between the N-methyl-nitrophthalimide and either the tolane or the HDE is advantageously carried out in a suitable solvent, for example, one consisting essentially of dimethyl sulfoxide or sulfolane, and toluene, or benzene, in about equal parts, by weight. More specifically, a reaction vessel is charged with either the tolane or HDE, a sufficient amount of aqueous sodium hydroxide is added to form the disodium salt of the particular dihydroxy compound in a mixture of, e.g., the toluene and dimethylsulfoxide. The mixture is advantageously heated to a temperature of about 60° to 75°C. for a time until the reaction is completed and the diimide is formed. Since a slight molar excess of about 5% of the N-methyl-nitrophthalimide is employed, it is desirable to remove this excess and thereby to isolate the bisimide of the particular dihydroxy reaction product. By treating the bisimide with an additional amount of aqueous sodium hydroxide in water at elevated temperatures, and then acidifying the reaction mass with hydrochloric acid, it is possible to obtain a tetraacid intermediate derivative which in turn can be subjected to heating at reflux with acetic acid and acetic anhydride, or by thermal dehydration at 175° to 200°C., to dehydrate the tetraacid to form the desired dianhydride.

In order that those skilled in the art may better understand how the present invention may be practiced, the following examples are given by way of illustration and not by way of limitation.

EXAMPLE 1

To a three-neck reaction vessel equipped with stirrer, reflux condenser, Dean-Stark water trap, and heating means was added 30 grams 1,2-bis(p-hydroxyphenyl)acetylene, 22.86 grams of 50% aqueous sodium hydroxide, 75 ml. toluene, and 75 ml. dimethylsulfoxide. The mixture was heated to 130°C. and stirred under nitrogen until the water-azeotrope which evolved stopped collecting. A calcium hydride trap was attached in place of the Dean-Stark trap and the last traces of moisture were eliminated. Under a stream of nitrogen at 60°C., 61.85 grams (5% molar excess) N-methyl-4-nitrophthalimide was added using 75 ml. anhydrous dimethyl sulfoxide and 75 ml. anhydrous toluene for the purpose of addition. The reaction mixture was stirred for 12 hours at about 60°C., after which the excess toluene was removed at reduced pressure, the mixture cooled and approximately 500 ml. of 1% aqueous acetic acid was added slowly to the residue. This mixture in turn was stirred for another 45 minutes and the obtained 4,4'-bisimide having the formula

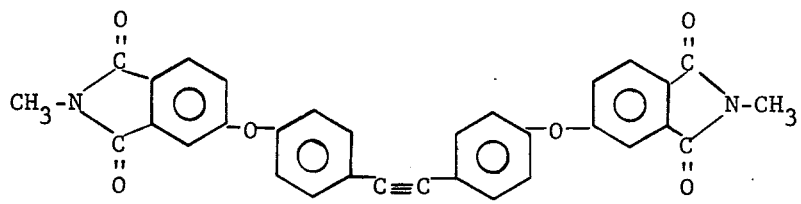

was filtered, washed with water, and dried at 90°C. in a vacuum oven to give the crude bisimide melting at 189°–191°C. About 76.16 grams of the bisimide was stirred with 300 ml. refluxing anhydrous CH₃OH for 10 minutes, and filtered to remove dimethyl sulfoxide to give 71.63 grams of the bisimide of formula VII. About 70 grams of the bisimide together with 63.59 grams of 50% aqueous sodium hydroxide and 200 ml. water were heated at the reflux temperature of the mass for 48 hours, cooled to room temperature and acidified with an excess of 1.2N hydrochloric acid. The mixture was again heated to reflux and stirred until the tetraacid crystallized. The mixture was cooled, filtered, and solid product dried for about 18 hours in a vacuum oven at 70°C. to give 72.5 grams of the corresponding tetraacid having the formula

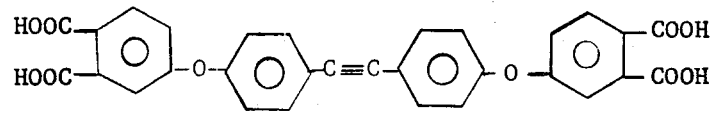

A mixture of 70.5 grams of the above tetraacid together with 280 ml. glacial acetic acid and 46.2 ml. acetic anhydride was heated with stirring under nitrogen at the reflux temperature of the mass for about 16 hours and then cooled to room temperature. The dianhydride which crystallized was recrystallized by dissolving it in 380 ml. dry toluene and 2.7 ml. acetic anhydride, stirred briefly at the reflux temperature, treated with 0.8 gram Norit, filtered, cooled, and the precipitated dianhydride dried at 90°C. for about 18 hours. The desired dianhydride of formula IV thus obtained had a melting point of 217°–218°C.

EXAMPLE 2

The dianhydride of formula V was prepared similarly as the dianhydride of formula IV described in Example 1. More particularly, to the same reaction vessel used in Example 1 was added 120 grams (0.427 mol) HDE, 68.32 grams of 50% aqueous sodium hydroxide, 600 ml. toluene and 600 ml. dimethylsulfoxide. The mixture was heated to 130°C. and stirred under nitrogen while removing the water azeotrope over a period of about 24 hours. A calcium hydride water trap was attached in place of the Dean-Stark water trap to remove the last traces of water from the reaction mixture. While maintaining the reaction mixture at 60°C. under a stream of nitrogen, 184.72 grams (5% molar excess) N-methyl-4-nitrophthalimide was added to the mixture and the latter stirred for 12 hours. Thereafter, the reaction mixture was fractionally distilled to remove the toluene under reduced pressure, cooled to room temperature, and 1,000 ml. of 1% aqueous acetic acid solution was slowly added to the reaction residue. The bisimide which settled out was filtered, washed with methanol, and dried in a vacuum oven at 70°C. for 24 hours. The yield of the bisimide thus obtained having the formula

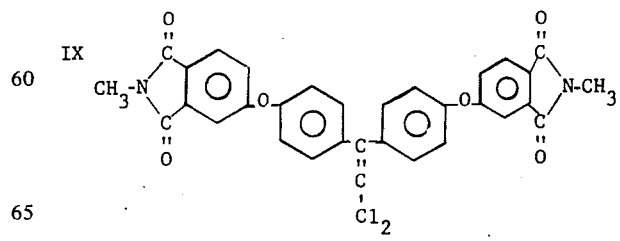

was equal to 250 grams. To a reaction vessel equipped with reflux condenser and stirrer were added 250 grams (0.417 mol) of the above-identified 4,4'-bisimide, 250 ml. 50% aqueous sodium hydroxide, and 500 ml. water. The mixture was heated at its reflux temperature for about 72 hours, cooled to room temperature and acidified with 1N hydrochloric acid. The aqueous acid solution was heated to reflux and stirred until the tetraacid separated out as an oil; the oil was removed and dissolved in 2 liters diethyl ether. The ether solution was washed with water (500 ml.), and then with a saturated sodium chloride solution and dried over anhydrous magnesium sulfate. Evaporation of the ether gave 208.8 grams of the solid tetraacid of the formula X 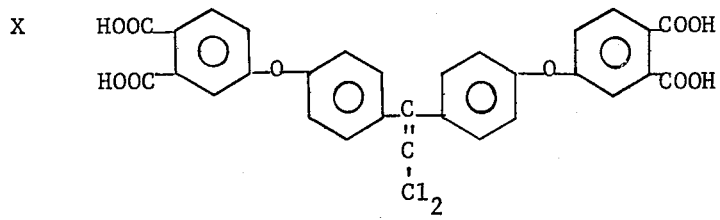

The dianhydride was prepared by adding 152 grams (0.25 mol) of the aforesaid tetraacid to a reaction vessel and the mixture was heated to 190°C. under reduced pressure for 2½ hours until the formation of water ceased. The dianhydride was cooled and taken up in toluene with 0.5% acetic anhydride. The toluene solution was treated with Norit, heated to reflux and filtered hot. After cooling, 128.26 grams of the desired crystalline dianhydride of formula V was obtained having a m.p. 100°C. The structure was confirmed by $^{13}C$ nmr.

EXAMPLE 3

The dianhydrides of formula I where the radicals of formulas II and III are in the 3-position on the dianhydride residues instead of the 4-positions, may be prepared similarly as in Examples 1 and 2 with the exception that instead of using N-methyl-4-nitro-phthalimide, one employs N-methyl-3-nitrophthalimide. By employing the above-described procedures, one will obtain the two anhydrides corresponding to the formula XI 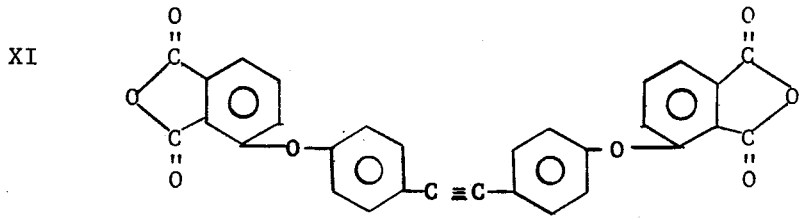

and

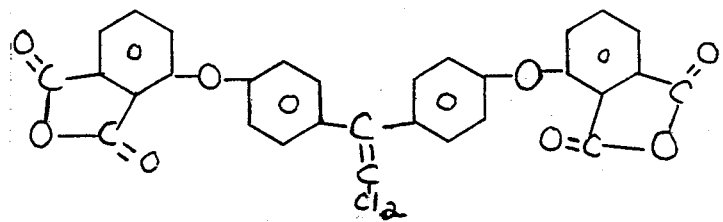

The above-described dianhydrides can be reacted with organic diamines, for example, 4,4'-diaminodiphenyl methane, m-phenyldiamine, 4,4'-diaminodiphenyl oxide, etc., to give polymers having extremely good high temperature and flame-retardant properties. Polyetherimide polymers derived in the above manner are more particularly disclosed and claimed in our copending application, Ser. No. 558,223, filed concurrently herewith and assigned to the same assignee as the present invention. By reference this application is made part of the disclosures of the instant application. The polyetherimides thus obtained can be used in various molding applications, for instance, as housings for appliances and for motors, as brake linings, etc., especially where heat resistance and other improved physical properties are essential. The dianhydrides can also be used to cure epoxy resins to produce flame retardant resinous compositions.

What we claim as new and desire to secure by Letters Patent of the United States is:

1. A composition of matter having the formula

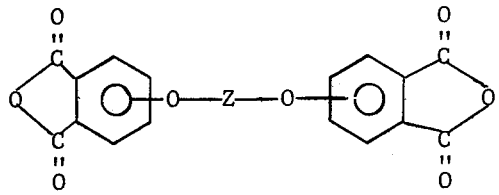

where Z is a member selected from the class consisting of the

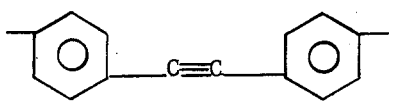

group and the

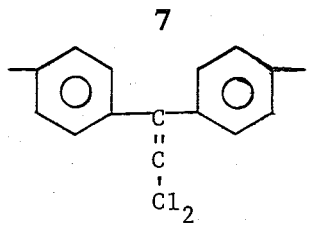
group.
2. A composition of matter having the formula
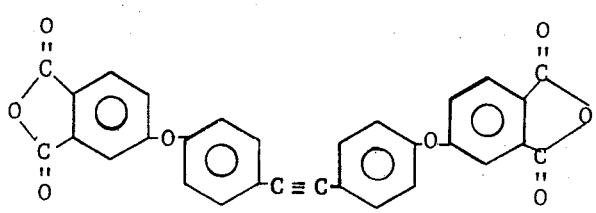
3. A composition of matter having the formula
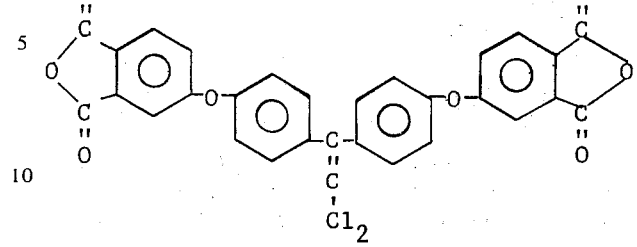
4. A composition of matter having the formula
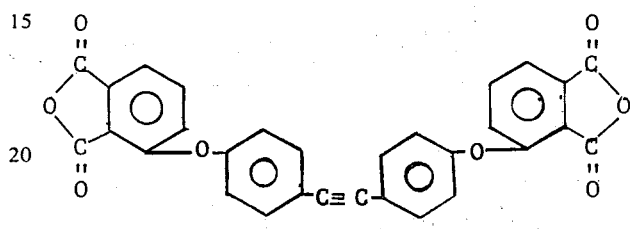
* * * * *